(12) United States Patent
Schlegel

(10) Patent No.: US 6,227,304 B1
(45) Date of Patent: May 8, 2001

(54) UPPER HITCH LINK

(75) Inventor: Daniel K. Schlegel, Salem, WI (US)

(73) Assignee: Case Corporation, Racine, WI (US)

( * ) Notice: Subject to any disclaimer, the term of this patent is extended or adjusted under 35 U.S.C. 154(b) by 0 days.

(21) Appl. No.: 09/259,871

(22) Filed: Mar. 1, 1999

(51) Int. Cl.$^7$ ................................... A01B 59/043
(52) U.S. Cl. ............... 172/439; 280/460.1; 280/461.1
(58) Field of Search .................. 172/439, 440, 172/441, 445.1, 451, 677, 679, 680; 280/460.1, 461.1

(56) References Cited

U.S. PATENT DOCUMENTS

| | | | |
|---|---|---|---|
| 2,565,337 | * | 8/1951 | Allan ............................... 172/439 X |
| 2,608,924 | | 9/1952 | Bywater et al. . |
| 3,145,781 | | 8/1964 | Rogler . |
| 4,181,181 | | 1/1980 | Old . |
| 4,186,811 | * | 2/1980 | Bidon .............................. 172/439 X |
| 4,194,756 | * | 3/1980 | Van Der Lely ...................... 172/439 |
| 4,424,870 | | 1/1984 | Weiss . |
| 4,436,162 | * | 3/1984 | Seibert ............................. 172/439 X |
| 4,519,623 | * | 5/1985 | Orthman ............................. 172/439 |
| 4,535,859 | * | 8/1985 | Van Der Lely ..................... 172/439 X |
| 4,659,102 | * | 4/1987 | Stuhrmann et al. .................. 280/481 |
| 4,773,666 | | 9/1988 | Koberlein et al. . |
| 4,899,831 | * | 2/1990 | Schillings et al. ................. 172/439 X |
| 5,423,394 | * | 6/1995 | Kendle ............................. 172/439 X |

OTHER PUBLICATIONS

LaForge Green Link 75—The LaForge Front 3 Point Hitch Specially Designed for the New John Deere Row Crop Tractors 7600–7700–7800 (Dec. 1993).
LaForge—The Necessary Link (Dec. 1993, Red Cover).
LaForge—The Necessary Link (Dec. 1993, Yellow Cover).
International Standard 8759/2—Agricultural wheeled tractors—Front–mounted linkage and power take–off, Part 2: Front linkage. First edition—1985–11–15.

\* cited by examiner

*Primary Examiner*—Victor Batson
(74) *Attorney, Agent, or Firm*—Foley & Lardner

(57) ABSTRACT

A work vehicle includes a front, first and second opposite sides extending rearwardly from the front, first and second lower links extending forward the front and an upper link above and between the first and second lower links. The first and second lower links have first end portions pivotably supported about a first axis and second end portions configured for being coupled to an implement. The upper link includes a tongue and first and second arms extending from the tongue. The first and second arms are spaced apart from one another and receive the front and first and second sides of the vehicle therebetween. The first and second arms are pivotably coupled to the vehicle to pivotably support the tongue about an axis rearward of the front of the vehicle.

35 Claims, 5 Drawing Sheets

UPPER HITCH LINK

FIELD OF THE INVENTION

The present invention relates to hitch assemblies, such as three-point hitch assemblies, utilized in work vehicles, such as wheeled and tracked tractors. In particular, the present invention relates to an upper link of a hitch mounted to a front of a work vehicle.

BACKGROUND OF THE INVENTION

Three point hitches are used by a variety of work vehicles, such as wheeled and tracked tractors, to attach an implement to the work vehicle and to raise or lower the implement relative to the work vehicle. Three point hitches generally include two spaced lower links and an upper link above and between the two lower links. Each of the upper link and lower links has an end configured for engaging and attaching the implement to the work vehicle. To lift the implement, the three point hitch generally includes one or more hydraulic cylinders, which directly or indirectly pivot the lower links to lower and raise the implement. As the implement is raised and lowered, the upper link stabilizes the implement and maintains the implement in a desired orientation relative to the work vehicle.

Three point hitches are generally either rear or front mounted. With rear-mounted three point hitches, the implement is secured to the vehicle at the rear of the vehicle and is pulled by the vehicle. In contrast, with front-mounted three point hitches, the implement is secured at the front end of the vehicle and is pushed by the vehicle. In many circumstances, work vehicles are provided with both rear and front-mounted three point hitches to simultaneously carry and utilize both front and rear implements.

Although similar to rear-mounted three point hitches, conventionally known front-mounted three point hitches have several unique operating characteristics and disadvantages because the three point hitch extends in front of the work vehicle. First, front-mounted three point hitches increase the length of the work vehicle. With conventional front-mounted three point hitches, the upper hitch link is pivotably supported about an axis at or forward the front of the work vehicle. Because the attachment point of the upper hitch link extends forward the front of the vehicle, the upper hitch link substantially increases the distance separating the operator from the forward most point of the work vehicle. As a result, the operator is also separated by a greater distance from a road intersection where visibility may be critical. In addition, the operator's general visibility may also be impaired due to perspective. For these reasons, many governmental bodies have enacted laws and regulations setting limits for the maximum distance that the operator may be separated or spaced from the forward most point of the work vehicle. For example, Europe includes regulations limiting the distance separating the forward most point of the vehicle and the front of the steering wheel to 3.5 meters. Larger work vehicles currently provided with front-mounted three point hitches or after market front-mounted three point hitches do not presently meet these regulations.

Second, because the front-mounted three point hitches are mounted at the front of the vehicle near the front axle, the implement carried by the three point hitch moves laterally as the work vehicle is being turned. Because the upper hitch link extends significantly forward the front of the work vehicle and significantly forward the front axle of the work vehicle, turning the work vehicle results in even larger lateral movements of the carried implement. Such large lateral movement is extremely undesirable when the implement being carried is in engagement with the ground.

Third, because the upper hitch link significantly extends forward the front of the work vehicle and forward the front axle, the mass of the implement carried by the hitch is even farther spaced from the front of the vehicle. As a result, larger loads are transmitted to the work vehicle. These larger loads reduce vehicle stability during both transport and field operation. Because the work vehicle must be designed to accommodate these larger loads, the manufacturing cost of the work vehicle is increased.

Thus, there is a continuing need for a front-mounted three point hitch which extends from the front of the work vehicle by a shorter distance to (1) reduce the distance separating the operator and the forward most point of the vehicle; (2) to enable larger work vehicles to meet governmental regulations limiting the maximum distance separating the forward most point of the work vehicle and steering wheel; (3) To reduce lateral movement of the three point hitch and the carried implement during turning of the work vehicle and (4) to couple the mass of the carried implement closer to the work vehicle to reduce manufacturing costs for the work vehicle.

SUMMARY OF THE INVENTION

The present invention provides an upper hitch link for use with a three-point hitch adapted for use with a work vehicle having a front and first and second opposite sides extending rearwardly from the front. The upper hitch link includes a tongue and first and second arms coupled to the tongue. The first and second arms are sufficiently spaced apart from one another to receive the front and the first and second sides of the work vehicle therebetween. The first and second arms are adapted to be pivotably coupled to the vehicle to pivotably support the tongue about a first axis rearward of the front of the vehicle. A substantial portion of the first and second arms extend rearward of the front of the vehicle.

The present invention also provides a hitch for use with a work vehicle having a longitudinal length, a front and first and second opposite sides extending rearwardly from the front. The hitch includes first and second lower links adapted to extend forward the front of the vehicle and an upper link adapted to be connected to the vehicle above and between the first and second lower links. The upper link includes first and second arms adapted to be pivotably coupled to the vehicle about a first axis rearward of the front of the vehicle, a cross bar interconnecting the first and second arms forward the front of the work vehicle and a tongue extending from the cross bar and configured to be coupled to an implement. The first and second arms are sufficiently spaced apart from one another to receive the front and the first and second sides of the vehicle therebetween. The cross bar extends substantially perpendicular to the longitudinal length of the vehicle.

The present invention also provides a work vehicle including a front, first and second opposite sides extending rearwardly from the front, first and second lower links extending forward the front, an actuator and an upper link. The first and second lower links have first end portions pivotably supported about a first axis and second ends configured for being coupled to an implement. The actuator is coupled to at least one of the first and second lower links and is configured to pivot the at least one of the first and second lower links about the first axis. The upper link includes a tongue and first and second arms extending from the tongue. The first and second arms are spaced from one another to receive a front and first and second sides of the vehicle therebetween. The first and second arms are pivotably coupled to the vehicle to pivotably support the tongue about a second axis rearward the front of the vehicle.

The present invention also provides a work vehicle including an operator station having a steering wheel hub, a front having a forward most point, first and second sides rearwardly extending from the front, and a front-mounted three-point hitch. The front-mounted three-point hitch includes first and second lower links extending forward the front, an upper link and an actuator coupled between the work vehicle and at least one of the first and second lower links and the upper link to pivot the front-mounted three-point hitch. The first and second lower links have first end portions pivotably supported about a first axis extending substantially rearward the forward most point of the front and second end portions configured for being coupled to an implement. The upper link includes a tongue and first and second arms extending from the tongue. The first and second arms are spaced from one another to receive the front and the first and second sides of the vehicle therebetween. The first and second arms are pivotablly coupled to the vehicle to pivotably support the tongue about a second axis rearward the front of the vehicle. The front-mounted three-point hitch has a forward most point that is longitudinally spaced from the hub by a distance of less than 3.5 meters when in a raised transport height.

DETAILED DESCRIPTION OF THE PREFERRED EMBODIMENTS

Figure 1:
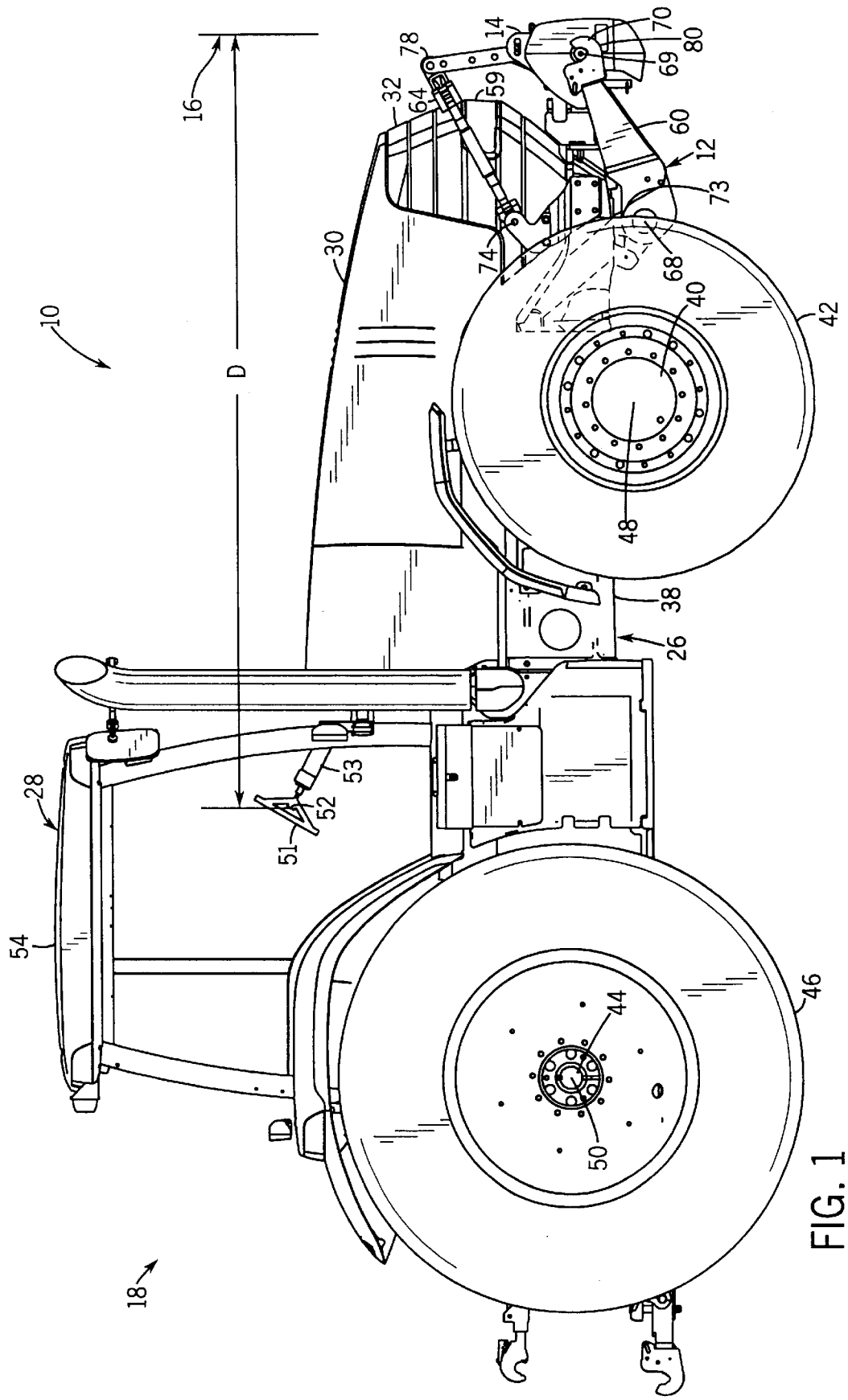
FIG. 1 is a side elevational view of the work vehicle including an exemplary embodiment of the front-mounted three-point hitch of the present invention coupled to a front weight package.

FIG. 1 is a side elevational view of a work vehicle 10, preferably a tractor, including front-mounted three-point hitch 12 supporting a front weight package 14. Work vehicle 10 comprises a conventionally known tractor having a longitudinal length between a front end 16 and a rear end 18 and a transverse width between sides 20, 22 (shown in FIG. 2). Work vehicle 10 generally includes chassis 26, operator station 28, hood 30 and front 32. Chassis 26 generally includes frame 38, front axle 40 supporting front wheels 42 and rear axle 44 supporting rear wheels 46. Frame 38 extends along an underside of work vehicle 10 and supports operator station 28 as well as the internal components of work vehicle 10 including its engine, transmission and hydraulic system (not shown). Frame 38 also supports axles 40 and 44 which rotatably support front wheels 42 and rear wheels 46 about axes 48 and 50, respectively, in a conventionally known manner. Operator station 28 is supported by chassis 26 and includes a seat and steering device, preferably a steering wheel 51 having a hub 52 and a steering column 53. Operator station 28 preferably additionally includes a cab 54 substantially enclosing the operator seat and the steering device.

Hood 30 is supported by frame 38 of chassis 26 and generally extends from operator station 28 towards front 32. Hood 30 at least partially extends about the engine of work vehicle 10. Front 32 extends at front end 16 of work vehicle 10 between hood 30 and frame 38. Front 32 includes a forward most surface or point 59 at a longitudinal end of the vehicle. Although not illustrated or described for purposes of brevity, front 32 may include such optional features as a bumper, a grill or headlights. In the exemplary embodiment, front 32 is a separate component mounted to frame 38 below hood 30 at front end 16. Alternatively, front 32 may be formed as part of hood 30 or may be formed from several individual components which are secured to one another or mounted adjacent one another to form front 32.

Three-point hitch 12 is supported by work vehicle 10 at front end 16. Three-point hitch 12 generally includes lower links 60, and upper link 64. Lower links 60, also known as draft links or draft arms, are pivotably coupled to work vehicle 10 for rotation about axis 68 which transversely extends between sides 20 and 22 of work vehicle 10 substantially rearward front end 16 of work vehicle 10. As best shown by FIG. 1, axis 68 preferably extends at a mid-point between front end 16 (i.e. the forward most point of front 32) and axis 48. Lower links 60 are generally configured to be as long as possible to flatten the arc about which the attached weight package 14 or an implement is pivoted. At the same time, lower link 60 must be coupled to work vehicle 10 so as to clear front tires 42 (or the front tracks if in a tracked work vehicle) and so as to preferably meet governmental regulations relating to the distance separating the forward most point 80 of hitch 12 and the operator, currently defined as the center hub 52 of steering wheel 51. This distance currently must be less than or equal to 3.5 meters. Lower links 60 extend forward from axis 68 and include ends 70 configured to be coupled to weight package 14 or an implement. Lower links 60 are pivoted about axis 68 by an actuator 88 (shown in FIG. 2) to raise and lower implement 14.

Upper link 64, also known as a top link, is pivotably coupled to work vehicle 10 about axis 74 substantially rearward of front end 16 of work vehicle 10 and the forward most point of front 32. In the exemplary embodiment, upper link 64 is pivotably coupled to work vehicle 10 about axis 74 which transversely extends slightly forward the forward most point 73 of tire 42 to clear tire 42 during turning. Upper link 64 extends forward from axis 74 to in front of front 32 at which point upper link 64 is pivotably coupled to implement 14 at axis 78. Upper link 64 preferably has a length extending between axes 74 and 78 equal to or slightly less than the length of lower links 60 extending between axes 68 and 69. As the difference between the length of upper link 64 and the length of lower links 60 increases, the kick angle also increases. Accordingly, upper link 64 has a length substantially equal to lower links 60, whereby axes 68 and 74 are in substantial longitudinal alignment with one another rearward front point 59 of front 32. Upper link 64 stabilizes implement 14 and maintains implement 14 in a desired vertical orientation. Upper link 64 cooperates with lower links 60 to lift, carry, push and pull implement 14 or other implements attached to both lower links 60 and upper link 64. Because upper link 64 is pivotably coupled to work vehicle 10 about axis 74 which lies substantially rearward of front end 16 of work vehicle 10 (i.e. the forward most point of front 32), upper link 64 extends a minimum distance in front 32 while having a minimum kick angle with respect to lower links 60. As a result, distance D separating the forward most point 80 of hitch 12 and the location of the center hub 52 of the steering wheel 51 of work vehicle 10 is minimized. In the exemplary embodiment, distance D, is less than or equal to 3.5 meters during transport. This distance of 3.5 meters is more specifically defined in German Reg. S&VO Section 30, Par. 4.7.3, the full disclosure of which is hereby incorporated by reference. As a result, work vehicle 10 with front-mounted three-point hitch 12 complies with governmental regulations limiting the maximum distance separating the forward most point of the work vehicle and the steering wheel. Moreover, because distance D is reduced, the operator of work vehicle 10 is located closer to road intersections and has improved visibility. Furthermore, because upper hitch link 64 extends a minimal distance forward of front 32, lateral movement of three-point hitch 12 and the implement 14 is reduced during turning of work vehicle 10. In addition, three-point hitch 12 enables the mass of implement 14 to be carried closer to work vehicle 10 to reduce loading placed upon work vehicle 10.

Figure 2:
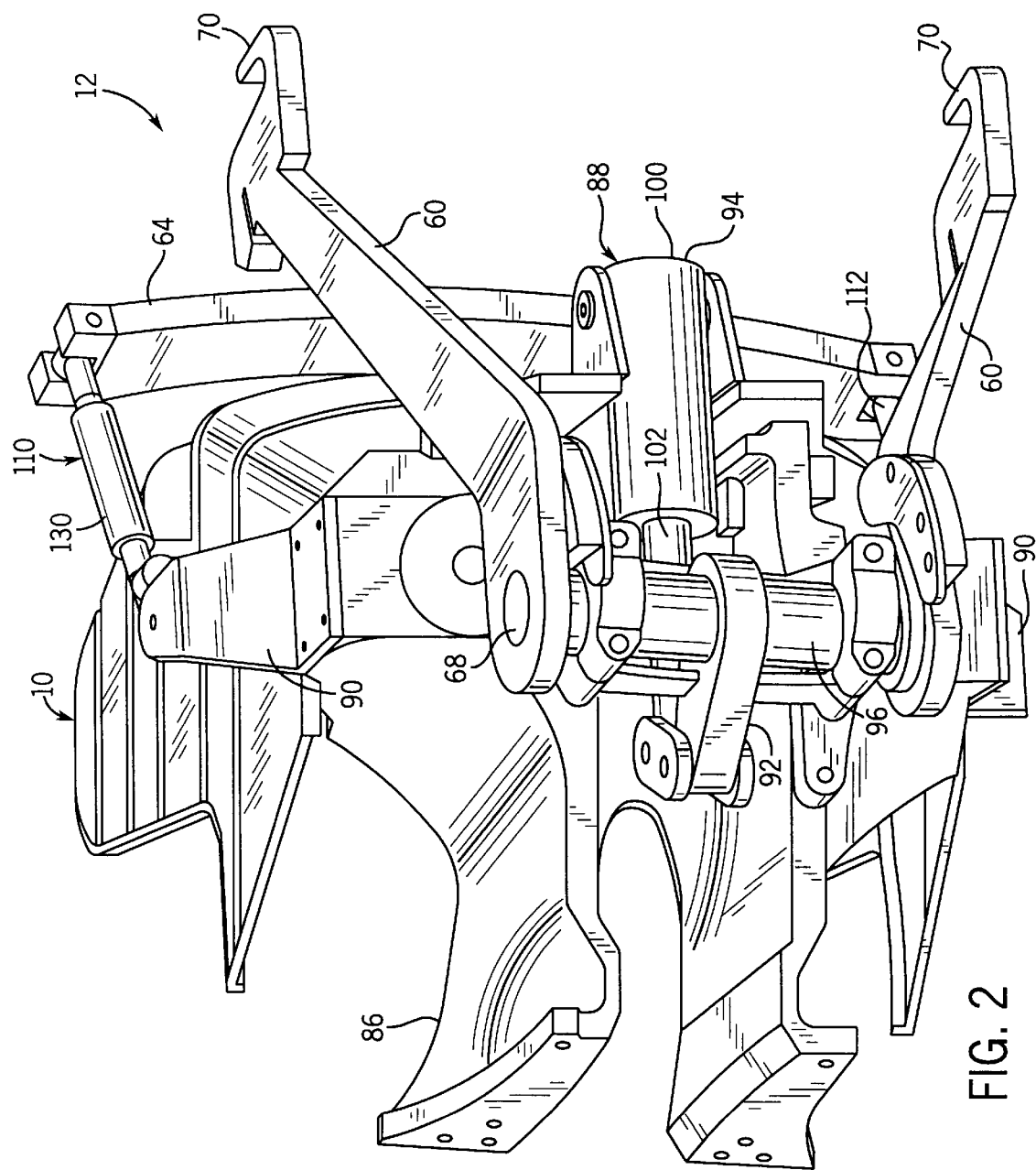
FIG. 2 is a bottom perspective of a front view of the work vehicle of FIG. 1 including the three-point hitch.
Figure 3:
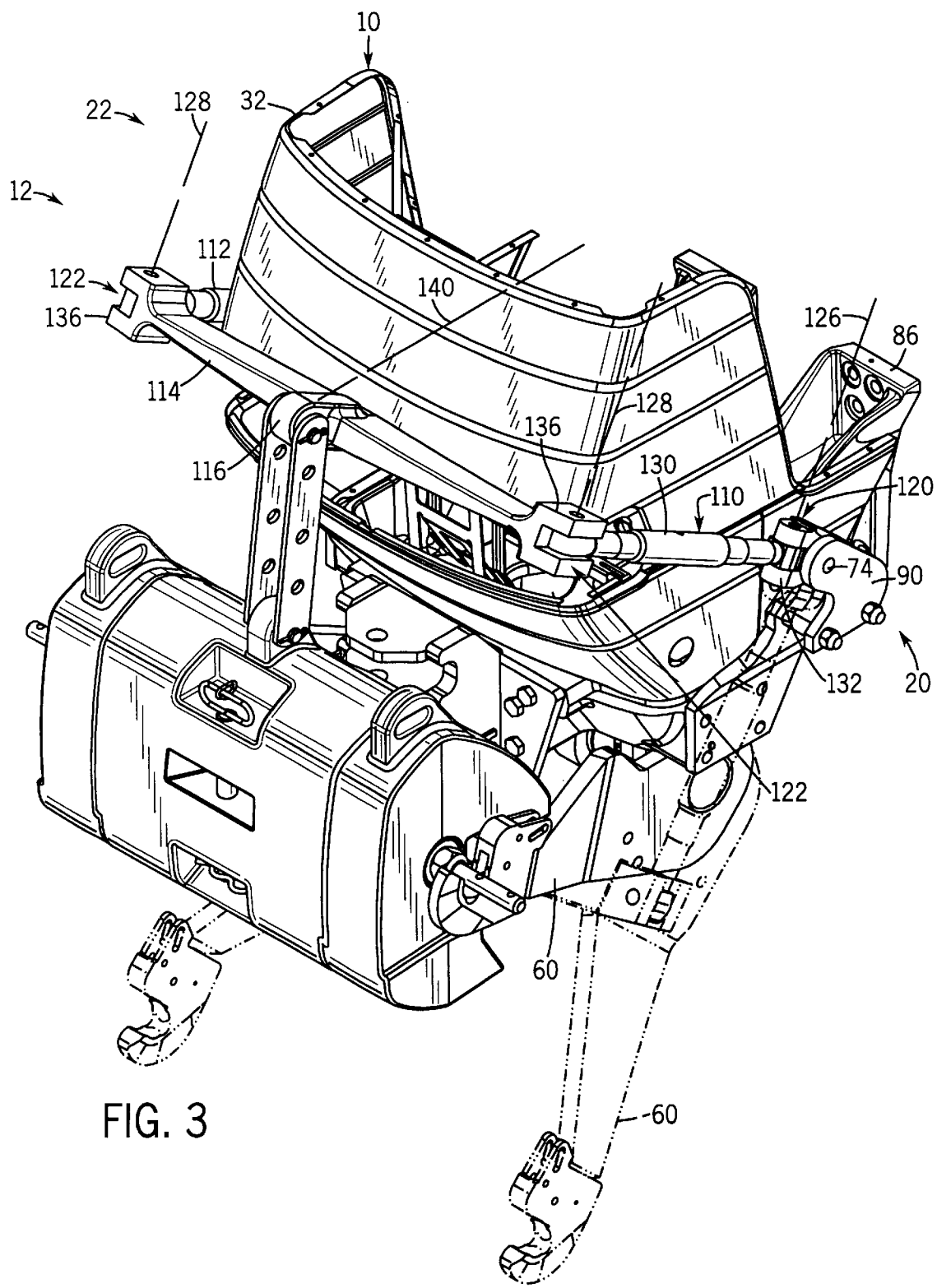
FIG. 3 is a front perspective view of a front of the work vehicle of FIG. 1 including the three-point hitch supporting the front weight package.
Figure 4:
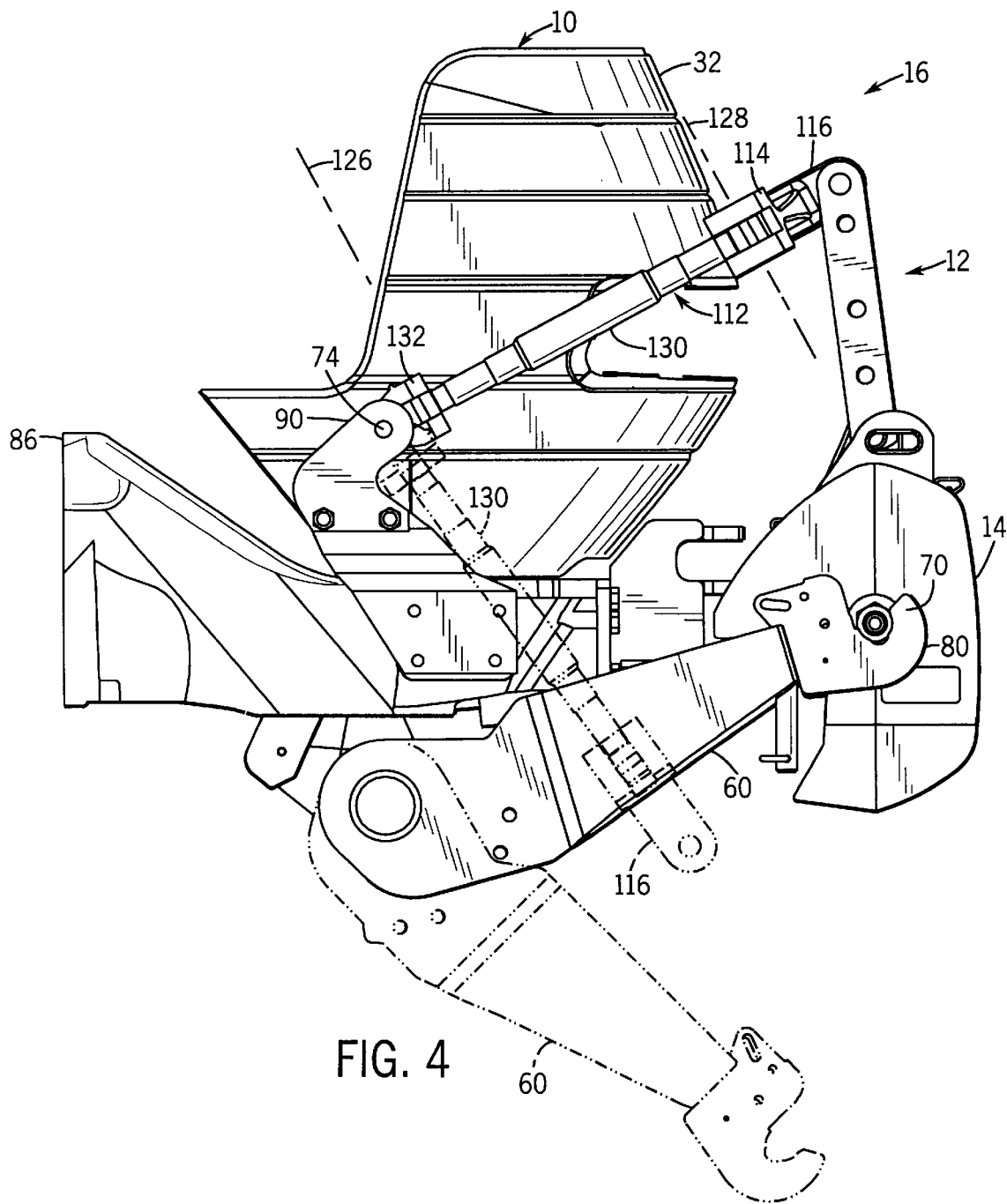
FIG. 4 is a side elevational view of the front of the work vehicle of FIG. 1 including the three-point hitch supporting the front weight package.
Figure 5:
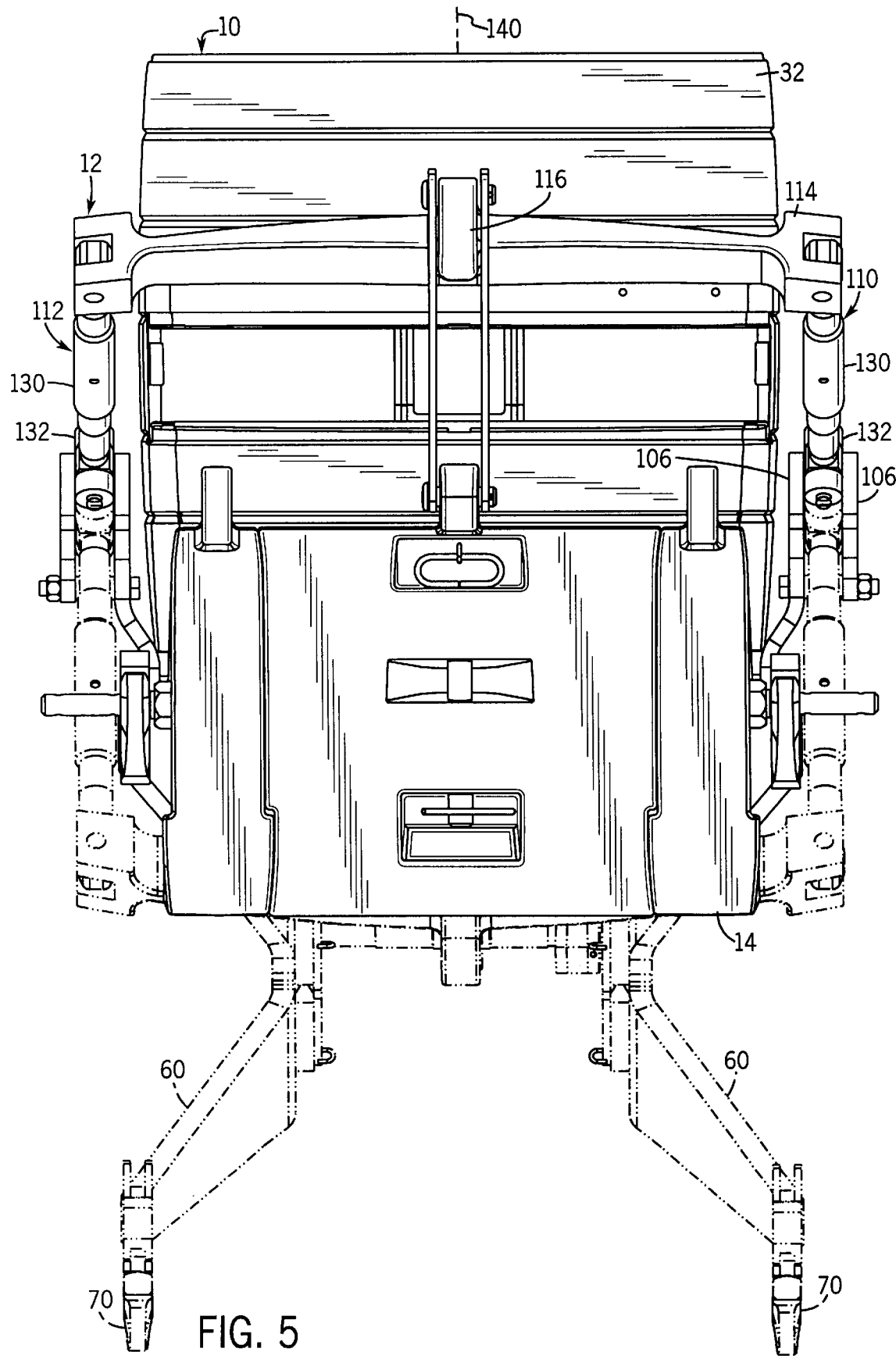
FIG. 5 is a front elevational view of the front of the work vehicle of FIG. 1 including the three-point hitch supporting the front weight package.

FIGS. 2–5 illustrate front-mounted three-point hitch 12 and front 32 of work vehicle 10 in greater detail. FIG. 2 is a bottom perspective view of hitch 12 and front 32; FIG. 3 is a side perspective view thereof; FIG. 4 is a side elevational view thereof; and FIG. 5 is a front elevational view thereof. As best shown by FIG. 2, in addition to lower link 60 and upper links 64, hitch 12 includes link support 86, rotary actuator 88 and upper link support brackets 90. Link support 86 comprises a structurally rigid load bearing member mounted to frame 38 (shown in FIG. 1) of work vehicle 10 at front end 16 below front 32. Support 86 supports lower link 60, rotary actuator 88, upper link support brackets 90 and upper link 64. Although support 86 is preferably cast as a single unitary member, support 86 may be formed by various methods and may comprise multiple components which are bolted, welded or otherwise secured to one another at front end 16 of work vehicle 10. Moreover, support 86 may be omitted where lower links 60, upper link 64 and rotary actuator 88 are directly supported by frame 38 of work vehicle 10.

Rotary actuator 88 is mounted to support 86 and is configured to pivot lower links 60 about axis 68. In the exemplary embodiment, rotary actuator 88 includes bell crank 92 and linear actuator 94. Bell crank 92 is coupled to shaft 96 extending between lower links 60 and pivotably supporting lower links 60 relative to support 86. Bell crank 92 is pivotably coupled to linear actuator 94. Linear actuator 94 preferably comprises a hydraulic cylinder assembly having a cylinder 100 and a piston 102. Cylinder 100 is stationarily mounted to work vehicle 10 while piston 102 is pivotably coupled to bell crank 92. Extension and retraction of piston 102 drives bell crank 92 to rotate shaft 96 and correspondingly rotate lower links 60. As will be appreciated, various other linear actuators may be used in lieu of the linear actuator 94. Moreover, although rotary actuator 88 is illustrated as including a linear actuator and a bell crank, various other rotary actuators may be employed for pivoting lower links 60 about axis 68.

Upper link support brackets 90 extend from support 86 on opposite sides 20 and 22 of work vehicle 10 to pivotably support upper hitch link 64 rearward of front end 16 of front 32. As best shown by FIG. 4, support brackets 90 each include a pair of spaced ears 106 which pivotably receive an end of upper hitch link 64 therebetween. Alternatively, other brackets or supports may be used for pivotably supporting upper hitch link 64 relative to work vehicle 10. Moreover, in lieu of comprising separate components which are bolted to support 86, support brackets 90 may alternatively be integrally formed with support 86, may be integrally formed with frame 38 (shown in FIG. 1), or may be mounted to other structural components of work vehicle 10 such as frame 38.

FIGS. 2–4 best illustrate upper hitch link 64. As shown by FIGS. 2–4, upper hitch link 64 includes arms 110, 112, cross bar 114 and tongue 116. Arms 110 and 112 extend along sides 20 and 22 of work vehicle 10, respectively. Preferably, arms 110, 112 extend substantially parallel to sides 20, 22 of work vehicle 10, respectively. Each arm 110, 112 has a first end 120 pivotably coupled to work vehicle 10 about axis 74 by bracket 90 and a second opposite end 122 coupled to cross bar 114. In the exemplary embodiment, ends 120 and 122 of arms 110 and 112 are further pivotably coupled to work vehicle 10 and cross bar 114, respectively, about vertically extending axes 126 and 128, respectively. Because ends 120 and 122 of arms 110 and 112 are each pivotably coupled to work vehicle 10 and cross bar 114 about vertically extending axes 126 and 128, arms 110 and 112 accommodate sway of cross bar 114. In particular, when hitch 12 is connected to an implement, such as implement 14, lower links 60 and upper link 64 are interconnected. In some instances, one of lower links 60 may become elevated with respect to the other. As a result, lower links 60 exert a force upon upper link 64 tending to cause upper link 64 to rotate and sway sideways towards either side 20 or 22 of work vehicle 10. The pivotable connection of ends 120 and 122 accommodates such sway.

In the exemplary embodiment, each of arms 110 and 112 include a main portion 130 and a trunion 132. Main portion 130 generally comprises a rigid rod or bar extending between ends 120 and 122 of arm 110. In the exemplary embodiment, a main portion 130 is preferably telescopically adjustable as to have an adjustable length. Trunion 132 receives main portion 130 at end 120 and is pivotably pinned to main portion 130 for pivotably supporting main portion 130 about axes 126. Trunion 132 is further pinned to bracket 90 to pivotably support main portion 130 about axis 74. As will be appreciated, arms 110 and 112 may be pivotably coupled to work vehicle 10 for rotation about axis 74 and axis 126 by various other well-known hinge or pivotable mounting structures. Moreover, although less desirable, arms 110 and 112 may alternatively be coupled to work vehicle 10 for pivotable rotation about only axis 74 if no elevational difference between links 60 is permitted.

As shown by FIG. 3, each arm 110, 112 has a length extending between axis 74 and cross bar 114. A majority of each length L of each of arms 110 and 112 extends along a side 20, 22 of work vehicle 10. In the exemplary embodiment, each arm 110, 112 has a length L of approximately 650 millimeters. Approximately 488 millimeters or 75% of each arm 110, 112 extends along sides 20, 22 of work vehicle 10. As a result, only a very minor portion of arms 110, 112 extend forwardly beyond front end 16 of front 32. Consequently, the length L of arms 110, 112 is relatively large to minimize the kick angle while minimizing the distance at which arms 110, 112 project in front of front 32.

Cross bar 114 comprises a substantially rigid bar or rod extending in front of front 32 of work vehicle 10 between sides 20 and 22. Cross bar 114 interconnects arms 110 and 112 and supports tongue 116. In the exemplary embodiment, cross bar 114 extends substantially perpendicular to both of sides 20 and 22 between sides 20 and 22. Consequently, cross bar 114 does not angle forward of front 32 and remains spaced from front end 16 of front 32 by a relatively short distance. As a result, cross bar 114 supports tongue 116 at a relatively short distance from front end 16 of front 32. In the exemplary embodiment, cross bar 114 is pivotally coupled to ends 122 of arms 110 and 112 for rotation about axes 128. To this end, cross bar 114 includes trunions 136 which are pinned to ends 122 of arms 110 and 112. As will be appreciated, cross bar 114 may be pivotably coupled to arms 110 and 112 by various alternative structures. For example, ends 122 of arms 110 and 112 could alternatively include trunions pivotably coupled to cross bar 114. As discussed above, because cross bar 114 is pivotally coupled to ends 122 of arms 110 and 112 about axes 128, upper hitch link 64 accommodates sideways swaying. Although less desirable, cross bar 114 may alternatively be fixedly coupled to ends 122 of arms 110 and 112 or may be integrally formed as part of a single unitary body with main portion 130 of arms 110 and 112.

Tongue 116 extends from cross bar 114 and is configured to be pivotally coupled to the mast of an implement, such as implement 14, or to an implement quick-coupling device which couples tongue 116 to an implement. Tongue 116 preferably extends from cross bar 114 so as to be coupled to an implement or a quick-coupler at transverse center line 140 of work vehicle 10. Tongue 116 generally extends forward from cross bar 114 by a minimal distance and defines an opening therethrough (not shown) by which an implement or a quick-coupler may be pivotably pinned thereto. In the exemplary embodiment, the front of the front of tongue 116, also the front of upper hitch link 64, extends forward of front 32 by a minimum distance of approximately 230 millimeters. The front of tongue 116 extends forward of front 32 by a maximum distance of approximately 350 millimeters. The front of tongue 116 extends approximately 130 millimeters forward of cross bar 114. As will be appreciated, the exact dimensions disclosed herein, such as those associated with arms 110, 112 and tongue 116, will vary depending on several factors. The present dimensions disclosed herein are for a 235 horsepower two-wheel drive tractor. Such dimensions will vary depending upon wheel base, steering wheel location, hood design and the front tires or tracks employed by the vehicle. In the exemplary embodiment, tongue 116 is integrally formed as part of a single unitary body with cross bar 114. Alternatively, tongue 116 may be bonded or otherwise affixed to cross bar 114 of various attachment methods such as welding, fasteners, adhesives and the like.

Overall, upper hitch link 64 enables front-mounted three-point hitch 12 to extend in front of work vehicle 10, and in particular, front end 16 of front 32, by a shorter distance as compared to conventional front-mounted three-point hitches. Because arms 110 and 112 pivot about axis 74 which extends substantially rearward of front end 16 of front 32 and because the majority of arms 110 and 112 extend along sides 20 and 22 of work vehicle 10, respectively, upper hitch link 64 has an increased length which provides a reduced kick angle while extending forward of front 32 by a minimal distance. Because cross bar 114 extends perpendicular to both arms 110 and 112 between arms 110 and 112 (i.e. transverse to the longitudinal length of work vehicle 10), cross bar 114 further supports tongue 116 at a minimal spacing from front end 16 of front 32. As a result, the distance separating the operator from the forward most point of tongue 116 is reduced to improve operator visibility at intersections and to enable work vehicle 10 to comply with governmental regulations limiting the maximum distance separating the forward most point of the work vehicle and the steering wheel. In addition, because upper hitch link 64 more closely couples the implement or the coupler to the front of work vehicle 10, lateral movement of three-point hitch 12 and implement 14 during the turning of work vehicle 10 is reduced. Furthermore, because upper hitch link 64 more closely couples the implement 14 to the front of work vehicle 10, the mass of implement 14 is also carried closer to the work vehicle to reduce loads placed upon work vehicle 10.

Although FIGS. 1–5 illustrate an exemplary embodiment of frontmount three-point hitch 12 configured for use on work vehicle 10, exact dimensions and configurations of hitch 12 may vary so long as hitch 12 meets the following criteria. First, the length of lower links 60 should preferably be as long as possible to flatten the path of the hitch point of links 60 as they are being pivoted. Second, the upper link 64 should preferably have a length extending between axes 74 and 78 approximately equal to or slightly less than the length of links 60 extending between axes 68 and 69 to reduce kick angle and insure that the kick angle is at least less than 15 degrees. Third, the forward most point of hitch 12, whether the forward most point of link 64 or the forward most point of link 60 should be longitudinally spaced from a median telescopic position of hub 52 by a distance of less than 3.5 meters. Fourth, the axes 68 and 74 must be located so to as to clear the front tire 42 during turning of tire 42 or the front of a track, when hitch 12 is employed on a tracked vehicle. Fifth, the axes 68 and 74 about which links 60 and link 64 pivot must be located so as to meet International Standards such as the maximum lower hitch point height above supporting surface, the minimum transport height and the minimum lower hitch point clearance set forth in International Standard 8759/2, the full disclosure of which is hereby incorporated by reference.

Although the present invention has been described with reference to preferred embodiments, workers skilled in the art will recognize that changes may be made in form and detail without departing from the spirit and scope of the invention. Because the technology of the present invention is relatively complex, not all changes in the technology are foreseeable. The present invention described with reference to the preferred embodiments and set forth in the following claims is manifestly intended to be as broad as possible. For example, unless specifically otherwise noted, the claims reciting a single particular element also encompass a plurality of such particular elements.

What is claimed is:

1. An upper hitch link for use with a three point hitch adapted for use with a work vehicle having a front, first and second opposite sides extending rearwardly from the front, and a front axle the upper hitch link comprising:

a tongue; and first and second arms coupled to the tongue, wherein the first and second arms are sufficiently spaced apart from one another to receive the front and the first and second sides of the work vehicle therebetween, wherein the first and second arms are adapted to be pivotably coupled to the vehicle to pivotably support the tongue such that the tongue pivots about a first axis rearward of the front of the vehicle and forward the front axle and wherein a substantial portion of the first and second arms extend rearward of the front of the vehicle.

2. The upper hitch link of claim 1 including a cross bar extending between the first and second arms and supporting the tongue.

3. The upper hitch link of claim 2 wherein the cross bar is mounted to the first and second arms.

4. The upper hitch link of claim 3 wherein the cross bar is pivotably coupled to each of the first and second arms.

5. The upper hitch link of claim 2 wherein the cross bar extends substantially perpendicular to the first and second arms.

6. The upper hitch link of claim 5 wherein the tongue extends substantially perpendicular to the cross bar.

7. The upper hitch link of claim 1 wherein the front axle is longitudinally spaced from the front of the work vehicle and wherein the first axis transversely extends between the first and second opposite sides halfway between the front of the work vehicle and the front axle.

8. The upper hitch link of claim 1 wherein the first and second arms each have a length extending forward from the first axis and wherein at least one-half of the length extends along the first and second opposite sides, respectively, of the work vehicle.

9. The upper hitch link of claim 1, wherein the tongue is adapted to extend forwardly away from the front of the vehicle and has a first rear end fixed against movement about a horizontal axis relative to the first and second arms and a second opposite end adapted to be pivotally coupled to an implement.

10. A hitch for use with a work vehicle having a longitudinal length, a front and first and second opposite sides extending rearwardly from the front, the hitch comprising:
    first and second lower links adapted to extend forward the front of the vehicle, the first and second lower links adapted to pivot about a first axis;
    an actuator coupled to at least one of the first and second lower links, the actuator being configured to pivot the first and second lower links about the first axis; and
    an upper link adapted to be connected to the vehicle above and between the first and second lower links, the upper link including:
        first and second arms adapted to be pivotably coupled to the vehicle about a second axis rearward of the front of the vehicle, wherein the first and second arms are sufficiently spaced apart from one another to receive the front and the first and second sides of the vehicle therebetween;
        a cross bar interconnecting the first and second arms forward the front of the work vehicle, wherein the cross bar extends substantially perpendicular to the longitudinal length of the work vehicle; and
        a tongue extending from the cross bar, wherein the tongue is configured to be coupled to an implement.

11. The hitch of claim 10 wherein the cross bar is mounted to the first and second arms.

12. The hitch of claim 11 wherein the cross bar is pivotably coupled to each of the first and second arms.

13. The hitch of claim 11, wherein the tongue has a first end fixed to the cross bar and a second opposite end adapted to be pivotally coupled to an implement.

14. The hitch of claim 10 wherein the tongue extends substantially perpendicular to the cross bar.

15. The hitch of claim 10 wherein the work vehicle includes a front axle longitudinally spaced from the front of the work vehicle and wherein the first axis transversely extends between the first and second opposite sides halfway between the front of the work vehicle and the front axle.

16. The hitch of claim 10 wherein the first and second arms each have a length extending forward from the first axis and wherein at least one-half of the length extends along the first and second opposite sides, respectively, of the work vehicle.

17. The hitch of claim 10, wherein the tongue pivots about the second axis.

18. A work vehicle comprising:
    a front;
    first and second opposite sides extending rearwardly from the front;
    a front axle;
    first and second lower links extending forward the front, the first and second links having first end portions pivotably supported about a first axis and second end portions configured for being coupled to an implement;
    an actuator coupled to at least one of the first and second lower links and configured to pivot at least one of the first and second lower links about the first axis; and
    an upper link including:
        a tongue; and
        first and second arms extending from the tongue, wherein the first and second arms are spaced from one another to receive the front and the first and second sides of the vehicle therebetween and wherein the first and second arms are pivotably coupled to the vehicle to pivotably support the tongue such that the tongue pivots about a second axis rearward the front of the vehicle and forward the front axle.

19. The work vehicle of claim 18 wherein the first and second axes about which the lower and upper links pivot extend within a substantially vertical plane.

20. The work vehicle of claim 18 including a steering wheel hub supporting a steering wheel, wherein the tongue is forwardly spaced from the steering wheel hub by less than approximately 3.5 meters.

21. The work vehicle of claim 18 including a cross bar extending between the first and second arms and supporting the tongue.

22. The work vehicle of claim 21 wherein the cross bar is mounted to the first and second arms.

23. The work vehicle of claim 22 wherein the cross bar is pivotably coupled to each of the first and second arms.

24. The work vehicle of claim 21 wherein the cross bar extends perpendicular to the first and second arms.

25. The work vehicle of claim 21 wherein the tongue extends substantially perpendicular to the cross bar.

26. The work vehicle of claim 18 wherein the front axle is longitudinally spaced from the front of the work vehicle and wherein the first axis transversely extends between the first and second opposite sides halfway between the front of the work vehicle and the front axle.

27. The work vehicle of claim 18 wherein the first and second arms each have a length extending forward from the axis and wherein at least one-half of the length extends along the first and second opposite sides, respectively, of the work vehicle.

28. The work vehicle of claim 18 wherein the first and second lower links are pivotably supported about a first axis substantially rearward the front of the work vehicle.

29. The work vehicle of claim 28 wherein the first axis about which the first and second lower links pivot is in substantial longitudinal alignment with the second axis about which the tongue is pivotably supported.

30. The work vehicle of claim 18, wherein the tongue extends forwardly from the front of the vehicle and has a first rear end fixed to the first and second arms against movement about a horizontal axis relative the first and second arms and a second opposite end adapted to be pivotally coupled to an implement.

31. A work vehicle comprising:
    an operator station including a steering wheel having a center hub;

a front having a first forward most point;

first and second opposite sides extending rearwardly from the front;

a front-mounted three-point hitch having a second forward most point and including:

first and second lower links extending forward the front, the first and second links having first end portion pivotably supported about a first axis rearward the first forward most point and second end portions configured for being coupled to an implement; and an upper link including:

a tongue;

first and second arms extending from the tongue, wherein the first and second arms are spaced from one another to receive the front and the first and second sides of the vehicle therebetween, wherein the first and second arms are pivotably coupled to the vehicle to pivotably support the tongue such that the tongue pivots about a second axis rearward the front of the vehicle wherein the second forward most point of the upper hitch link is longitudinally spaced from the hub by a distance less than 3.5 meters wherein the tongue extends forwardly away from the front of the vehicle and has a first rear end fixed to first and second arms against movement about a horizontal axis relative the first and second arms and a second opposite end adapted to be pivotally coupled to an implement; and an actuator coupled between the work vehicle and at least one of the first and second lower links and the upper link to pivot the front mounted three-point hitch.

32. The work vehicle of claim 1 wherein the actuator is coupled to at least one of the first and second lower links, the actuator being configured to pivot the first and second lower links about the first axis.

33. A hitch for use with a work vehicle having a longitudinal length, a front and first and second opposite sides extending rearwardly from the front, the hitch comprising:

first and second lower links adapted to extend forward the front of the vehicle; and an upper link adapted to be connected to the vehicle above and between the first and second lower links, the upper link including:

first and second arms adapted to be pivotably coupled to the vehicle about a first axis rearward of the front of the vehicle, wherein the first and second arms are sufficiently spaced apart from one another to receive the front and the first and second sides of the vehicle therebetween;

a cross bar interconnecting the first and second arms forward the front of the work vehicle, wherein the cross bar extends substantially perpendicular to the longitudinal length of the work vehicle;

a tongue extending from the cross bar, wherein the tongue is configured to be coupled to an implement; and a front axle longitudinally spaced from the front of the work vehicle, wherein the first axis transversely extends between the first and second opposite sides halfway between the front of the work vehicle and the front axle.

34. An upper hitch link for use with a three point hitch adapted for use with a work vehicle having a front and first and second opposite sides extending rearwardly from the front, the upper hitch link comprising:

a tongue; and first and second arms coupled to the tongue, wherein the first and second arms are sufficiently spaced apart from one another to receive the front and the first and second sides of the work vehicle therebetween, wherein the first and second arms are adapted to be pivotably coupled to the vehicle to pivotably support the tongue such that the tongue pivots about a first axis rearward of the front of the vehicle, wherein a substantial portion of the first and second arms extend rearward of the front of the vehicle and wherein the tongue is adapted to extend forwardly away from the front of the vehicle and has a first rear end fixed against movement about a horizontal axis relative to the first and second arms and a second opposite end adapted to be pivotally coupled to an implement.

35. A work vehicle comprising:

a front;

first and second opposite sides extending rearwardly from the front;

first and second lower links extending forward the front, the first and second links having first end portions pivotably supported about a first axis and second end portions configured for being coupled to an implement;

an actuator coupled to at least one of the first and second lower links and configured to pivot at least one of the first and second lower links about the first axis; and an upper link including:

a tongue; and first and second arms extending from the tongue, wherein the first and second arms are spaced from one another to receive the front and the first and second sides of the vehicle therebetween, wherein the first and second arms are pivotably coupled to the vehicle to pivotably support the tongue such that the tongue pivots about a second axis rearward the front of the vehicle and wherein the tongue extends forwardly from the front of the vehicle and has a first rear end fixed to the first and second arms against movement about a horizontal axis relative the first and second arms and a second opposite end adapted to be pivotally coupled to an implement.

* * * * *